United States Patent [19]

Chen et al.

[11] Patent Number: 5,567,824
[45] Date of Patent: Oct. 22, 1996

[54] PALLADIUM CATALYZED RING CLOSURE OF TRIAZOLYLTRYPTAMINE

[75] Inventors: Cheng Y. Chen, Colonia; Robert D. Larsen, Bridgewater; Thomas R. Verhoeven, Cranford, all of N.J.

[73] Assignee: Merck & Co., Inc., Rahway, N.J.

[21] Appl. No.: 248,288

[22] Filed: May 24, 1994

[51] Int. Cl.$^6$ ................................. C07D 401/12
[52] U.S. Cl. ........................ 548/252; 548/266.4
[58] Field of Search .................. 548/252, 266.4

[56] References Cited

U.S. PATENT DOCUMENTS 5,298,520  3/1994  Baker et al. ................ 514/383

FOREIGN PATENT DOCUMENTS

| 0497512A3 | 8/1992 | European Pat. Off. . |
| 0548813A1 | 6/1994 | European Pat. Off. ...... C07D 401/12 |
| 94/02476 | 2/1994 | WIPO . |

OTHER PUBLICATIONS

Chem Abstracts, vol. 116, No. 19, Ab. No. 194092p, "Conversion of 2–iodoaniline . . . " by Luo, F. T. et al., May 11, 1992.
Tetrahedron Letters, vol. 35, No. 38, pp. 6981–6984, (1994) "Synthesis of the 5–HT1D Receptor Agonist . . . " C. Y. Chen et al.
B. A. Astleford et al., J. Org. Chem., vol. 54, pp. 731–732 (1989).
D. Wensbo et al., Tetrahedron Letters, vol. 34, No. 17, pp. 2823–2826, (1993).
T. Jeschke et al., Tetrahedron Letters, vol. 34, No. 40, pp. 6471–6474, (1993).
R. C. Larock et al., J. Am. Chem. Soc., vol. 113, pp. 6689–6690 (1991).

Primary Examiner—Jacqueline Haley
Attorney, Agent, or Firm—Robert J. North; Melvin Winokur

[57] ABSTRACT

A new process is described for the synthesis of the triazolyl tryptamine:

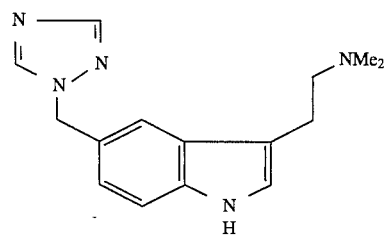

and related compounds. The process involves a palladium-catalyzed ring closure between a substituted ortho-iodoaniline and a protected 1-alkynol. The process is carried out at high temperature, e.g. 100° C., in a dry inert solvent, e.g., DMF and in the presence of a proton acceptor, e.g., $Na_2CO_3$ or a trialkylamine. The triazolyl tryptamine, as well as acid addition salts thereof, is a 5 $HT_1D$ receptor agonist having anti-migraine properties.

21 Claims, No Drawings

PALLADIUM CATALYZED RING CLOSURE OF TRIAZOLYLTRYPTAMINE

BACKGROUND OF THE INVENTION

1. Field of the Invention

The present invention relates to the preparation of a class of 5-heterocyclic substituted tryptamines, e.g., 5-( 1, 2, 4-triazol-1-yl) tryptamine, compounds, therapeutically active as anti-migraine agents. The invention concerns an improved process for producing these 5-heterocyclic substituted tryptamine derivatives which involves a palladium-catalyzed coupling and ting closure.

2. Brief Description of Disclosures in the Art

The complex physiological and pathophysiological processes of the neurotransmitter serotonin (5-HT) are becoming increasingly elucidated.[1] (Superscripted References are listed in the back). In one role, serotonin acts as a vasoconstrictor in the brain and, thereby, displays beneficial properties in migraine therapy. Its potential as a pharmaceutical agent, however, is limited due to its rapid metabolism in vivo. Over the past few years an extensive effort has been devoted to the development of N,N-dialkyltryptamines as $5\text{-HT}_{1D}$ receptor agonists to achieve the desired activity and selectivity for the treatment of migraine. Sumatriptan is the first of this class of drugs to be approved for this purpose.[2] MK-0462 (developed by Merck & Co.), is described in U.S. Pat. No. 5,298,520 and is also a potent $5\text{-HT}_{1D}$ receptor agonist that is undergoing clinical studies.

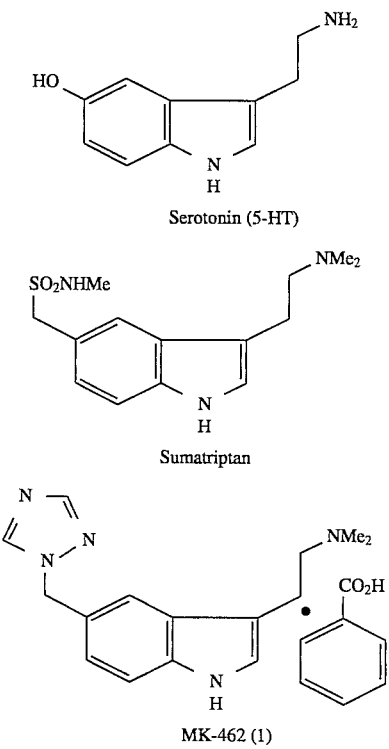

Generally, this class of compounds is made by the Fisher indole reaction for the preparation of the N,N-dimethyltryptamine framework. Application of this methodology to the synthesis of MK- 0462, however, is ineffective and low-yielding due to the instability of the benzyl triazole moiety to the reaction conditions, which generally leads to polymerization of the triazole moiety, producing oligomers. What is desired in the art is a highly efficient method for the preparation of the N,N-dimethyltryptamine, MK-0462 (1) which eliminates the undesirable tendency of triazole polymerization.

Larock et at., have shown that coupling of an iodoaniline species with an internal acetylene using palladium catalysis gives 2,3-disubstituted indoles in good-to-excellent yields.[3] Smith et al., have also demonstrated this for 4-pyrimidinyl and pyridinyl derivatives of indol-3-yl-alkyl piperazines as in published EP0 548 831 A1. Two other applications of this methodology have been demonstrated in the syntheses of hetero-condensed pyrroles[4a] and tryptophans[4b]. However, all of these methods require triphenylphosphine, as part of the catalyst system, which is an environmental hazard.

The application of palladium-catalyzed coupling methodology to the specific synthesis of the 5-triazolyl N,N-dimethyltryptamine ring system, has not been reported previously.

SUMMARY OF THE INVENTION

We have found that MK-462 can be synthesized in high yield by the palladium-catalyzed coupling/ring closure of a 3-iodo-4-aminobenzyltriazole with a suitably protected butynol derivative to the corresponding tryptophol, followed by conversion of the hydroxyethyl moiety to a dimethylaminoethyl. The advantages of this new process are that it does not require the use of triphenylphosphine, and also tetrabutylammonium chloride and lithium chloride and it also eliminates the tendency of triazolyl polymerization as experienced in the Fischer Indole Synthesis. In general, the process can be used to prepare 5-substituted tryptamines where the 5-substituent is triazolyl, triazolylmethyl, imidazolyl, imidazolylmethyl, tetrazolyl, or tetrazolylmethyl.

By this invention there is provided a process comprising the step of contacting a compound of Structure I with a compound of Structure II to form a compound of Structure III:

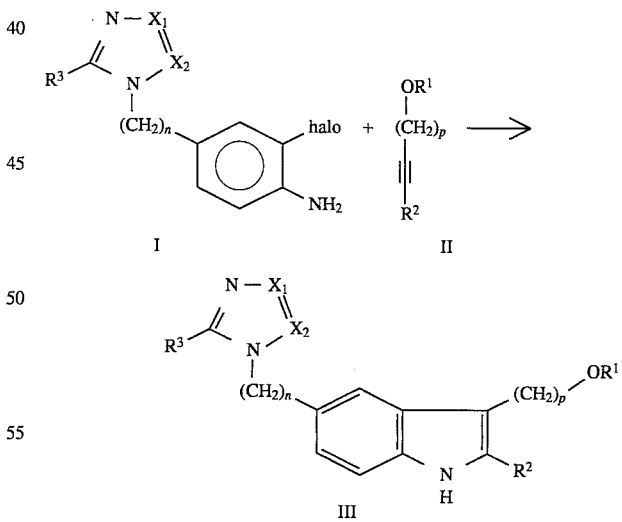

said process being carried out in a dry inert organic solvent for Structures I and II, at a temperature in the range of about 70° to 120° C., in the presence of a palladium catalyst, soluble in said solvent, present in an amount of 0.5 to 5 mole percent relative to I, and in the presence of an inorganic or organic amine compound which functions as a proton acceptor, i.e., acid scavenger, and does not chemically react with said catalyst, wherein:

X₁ and X₂ are independently ting nitrogen or carbon atoms;

halo represents Br or I;

n is an integer from 0–1;

p is an integer from 1–4;

$R^3$ is H or linear or branched $C_1$–$C_4$ alkyl;

$R^1$ is H or a radical which functions as a hydroxy protecting group, which is removable, under mild acid hydrolyses, for example, by contacting with a mixture of HCl/MeOH, e.g. 1:12 N HCl/MeOH, at 0°–30° C.;

$R^2$ is a radical which functions as a terminal acetylene carbon protecting group, which is removable by mild acid hydrolysis, for example, by contacting with a mixture of HCl/MeOH, e.g. 1:12 N HCl/MeOH at 0°–30° C.

DESCRIPTION OF THE INVENTION AND PREFERRED EMBODIMENTS

The synthesis of MK-462 (1) is illustrated in the following Scheme 1 below.

A key element of the synthesis is the production of the tryptophol precursor 7, which can be prepared by coupling of 3-iodo-4-aminobenzyltriazole 3 with a suitably protected butynol derivative 5.

SCHEME 1

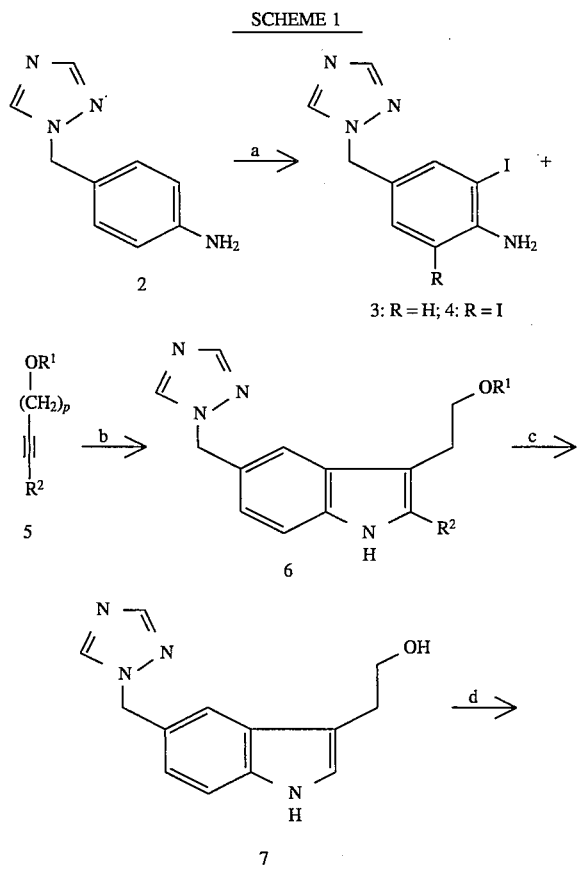

-continued
SCHEME 1

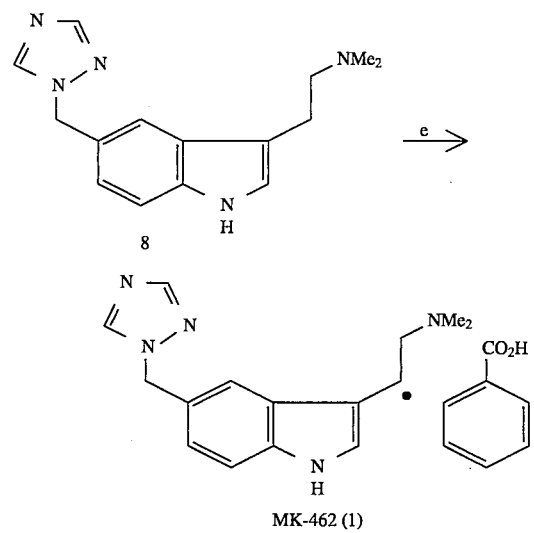

The synthesis of MK-462 (1) begins with the preparation of the iodoaniline 3. 4-Aminobenzyltriazole 2 is available in 3 steps and >90% overall yield from 4-nitrobenzyl bromide and 4-amino-1,2,4-triazole using a modified literature procedure.[5] Reaction of 2 with iodine monochloride in the presence of $CaCO_3$ in aqueous methanol furnishes the 4-triazolyliodoaniline 3 in 91% yield; some over-iodination occurs to provide 1%–3 % of the diiodoaniline 4. The over-iodination is not difficult to control since it occurs much more slowly.

The palladium-catalyzed coupling/ring closure between the iodoaniline 3 and the butynol 5 was found to proceed smoothly in surprisingly high yield in the absence of the standard required reagents triphenylphosphine, tetrabutylammonium chloride, and lithium chloride, and in the absence of any triazolyl-induced polymerization.

The coupling reaction between the iodoaniline 3 and various derivatives of 3-butyn-1-ol was intimately studied in detail (Table 1 below). In order to prevent coupling at the terminal carbon of the acetylene, it was found that silyl protection was necessary.[3] The silyl groups were incorporated by formation of the dianion with BuLi followed by quenching with two equivalents of the silyl chloride. In the case of the TBDMS-protected (tertiary butyl-dimethylsilyl) alkyne, the bis-silylation unexpectedly did not go to completion; rather, a 1:1 mixture of 5d and 5e resulted. It was found that alternative O-protection could be carried out by selective hydrolysis of the O-silyl group; for example, 5a was convened to 5b in quantitative yield using dilute HCl in aqueous methanol. The hydroxy group of 5c can then be protected with the TBDMS or THP group to afford the alkynes 5f and 5g, respectively, in quantitative yields.

TABLE 1

| Effect of Butynol Protection on Yield of Coupling[a] | | |
|---|---|---|
| Entry | Acetylenes | Yields of Indoles |
| 1 | 5a $R^1$, $R^2$ = $SiEt_3$ (TES) | 6a + 6b (80%) |
| 2 | 5b $R^1$ = H, $R^2$ = $SiEt_3$ | 6b (74%) |
| 3 | 5c $R^1$ = H, $R^2$ = $SiMe_3$ | 6c (56%) |
| 4 | 5d $R^1$, $R^2$ = TBDMS | 6d (78%) |
| 5 | 5e $R^1$ = H, $R^2$ = TBDMS | 6e (60%) |
| 6 | 5f $R^1$ = TBDMS, $R^2$ = TMS | 6f (77%) |

TABLE 1-continued

Effect of Butynol Protection on Yield of Coupling[a]

| Entry | Acetylenes | Yields of Indoles |
|---|---|---|
| 7 | 5g $R^1$ = THP, $R^2$ = TMS | 6g (79%) |

[a]Conditions: 2 mol % Pd(OAc)$_2$, Na$_2$CO$_3$, DMF, 100° C.; Ratio of 3/5 = 1:1.05–1.2. Me = methyl, Et = ethyl, TBDMS = t-butyldimethylsilyl, TMS = trimethylsilyl, TES = triethylsilyl, THP = tetrahydropyranyl.

The simplest derivative 5c couples with the iodoaniline 3 to afford the 2-TMS-indole 6c in 56% yield.[6] The undesired regioisomer 9 (5%) is also formed (See below in Chart 1). Other undesired impurities are also formed. The TMS group is believed to be responsible for these byproducts and the low yield. We surprisingly found that the more stable TES and TBDMS groups on the alkyne give indoles 6a and 6d[8], respectively, in higher yields (Entries 1 and 4). Although the more stable C-protection gives better results, the bully TBDMS butyne couples considerably slower; therefore we found that TES is a particularly useful protecting group in this specific synthesis because it offers a suitable rate of coupling and stability.

CHART 1

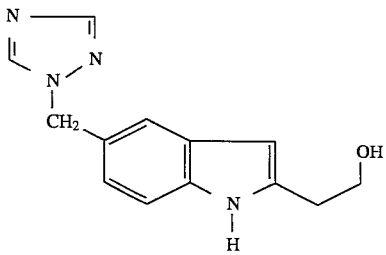

9

Desilylation of the combined indoles 6a and 6b in MeOH-HCl affords tryptophol 7[8] in 70%–80% overall yield after work-up and crystallization (Scheme 1). Desilylation of 2-silylated-indoles can also be carded out with other acids such as alkanoic acids, AlCl$_3$, methanesulfonic acid and other sulfonic acids. However, we found that the system MeOH-HCl is decidedly more useful and convenient to use particularly from an environmental standpoint. Conversion of 3 and 5a to 7 is carded out directly without isolation of 6. In the crystallization of 7 the regioisomer 9 (6%) is removed in the mother liquor.

Conversion of the tryptophol 7 to MK-0462 (1) involves the formation of mesylate from tryptophol 7 followed by the dimethylamine displacement to afford MK-0462 free base 8[8] in 79% yield. We unexpectedly found that the mesylate is prone to polymerization from intermolecular alkylation by the triazole; therefore, the mesylate is treated directly with 40% dimethylamine. The isolated tryptamine is then purified by addition of a solution of benzoic acid to the free base to afford the MK-0462 as a benzoate salt in 95% yield.

This new synthesis of MK-0462 (1) featuring a palladium-catalyzed coupling of the iodoaniline 3 and the bis-TES-butynol 5a to form the indole ting is an efficient process amenable to scale up that despite formation of several impurities, unexpectedly requires no chromatographic purifications as contrasted to the standard Fischer Indole Synthesis.

REFERENCES AND NOTES

1 Glennon, R. A.; Darmani, N. A.; Martin, B. R. Life Sciences 1991, 48, 2493.

2. (a) Feniuk, W.; Humphrey, P. P. A. Drug Der. Res. 1992, 26, 235; (b) Hopkins, S. J. Drug of Today 1992,28, 155.

3. Larock, R. C; Yum, E. K. J. Am. Chem. Soc. 1991, 113, 6689.

4. (a) Wensbo, D.; Eriksson, Jeschke, T.; Annby, U.; Gronowitz, S.; Cohen, L. A. Tetrahedron Lett. 1993, 34, 2823. Co) Wensbo, D.; Eriksson, Jeschke, T.; Annby, U.; Gronowitz, S.; Cohen, L. A. Tetrahedron Lett. 1993, 34, 6471.

5. Astleford, B. A, Goe, G. L; Keay, J. G.; Scriven, E. F. V. J. Org. Chem. 1989, 54, 731–732.

6. (a) 5c was purchased from Farchan Laboratories. (b) Pd(OAc)$_2$ was purchased from Johnson-Matthey.

8. All new compounds were characterized by $^1$H NMR, $^{13}$C NMR and elemental analysis. Selective data ($^1$H NMR at 250 MHz, $^{13}$C NMR at 62.5 MHz): Indole 6b: $^1$H NMR (CDCl$_3$) δ 0.90 (m, 15 H), 1.60 (t, J =5.2 Hz, 1H), 3.09 (t, J = 7.9 Hz, 2H), 3.85 (dt, J = 7.9, 5.2 Hz, 2H), 5.40 (s, 2H), 7.10 (dd, J=8.3, 1.4 Hz, 1H), 7.35 (d, J=8.3 Hz, 1H), 7.60 (d, J = 1.4 Hz, 1H), 7.92 (s, 1H), 7.98 (s, 1H), 8.10 (s, 1H); 13C NMR (MeOH-d$_4$) δ 152.1, 144.5, 140.5, 134.0, 130.3, 126.2, 123.0, 122.3, 119.9, 112.7, 64.5, 55.3, 30.9, 7.9, 4.6; Anal. Calcd for C$_{19}$H$_{27}$N$_5$OSi: C, 64.18; H, 7.66; N, 15.76. Found: C, 63.81; H, 7.87; N, 16.15.

Tryptophol 7: mp 131°–132° C.; $^1$H NMR (DMSO-d$_6$) δ 2.81 (t, J=7.4 Hz, 2H), 3.63 (dt, J = 7.4, 5.3 Hz, 2H), 4.65 (t, J =5.3 Hz, 1H), 5.43 (s, 2H), 7.00 (rid, J=8.4, 1.4 Hz, 1H), 7.15 (d, J = 2.0 Hz, 1H), 7.51 (s, 1H), 7.94 (s, 1H), 8.62 (s, 1H), 10.85 (s, 1H); 13C NMR (DMSO-d$_6$) δ 151.3, 143.6, 135.7, 127.3, 125.8, 123.6, 121.1,118.3, 111.7, 111.4, 61.5, 53.0,.28.7; Anal. Calcd for C$_{13}$H$_{14}$N$_4$O: C, 64.44; H, 5.82; N, 23.12. Found: C, 64.38; H, 5.85; N, 23.28.

Tryptamine 8: mp 120°–121° C.; $^1$H NMR (DMSO-d$_6$) δ 2.34 (s, 6H), 2.63 (m, 2H), 2.93 (m, 2H), 5.43 (s, 2H), 7.05 (m, 2H), 7.31 (d, J=8.3 Hz, 1H), 7.56 (s, 1H), 7.97 (s, 1H), 7.99 (s, 1H), 8.49 (s, 1H); $^{13}$C NMR (CDCl$_3$) 151.7, 142.8, 136.4, 127.7, 124.5, 123.1,121.9, 119.1, 113.9, 112.0, 60.2, 54.6, 45.3, 23.5; Anal. Calcd for C$_{15}$H$_{19}$N$_5$: C, 66.89; H, 7.11; N, 26.00. Found: C, 66.89; H, 7.20; N, 26.04.

The above described specific synthesis of MK-462 can also be extended to other active analogs containing an imidazole, triazole or tetrazole in the indole 5-position attached through a ring nitrogen atom, through a methylene group, or attached directly to the 5-position of the indole ring as illustrated in the following flow scheme:

FLOW SCHEME

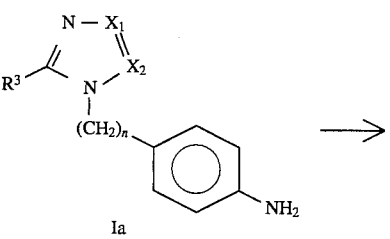

Ia

-continued
FLOW SCHEME

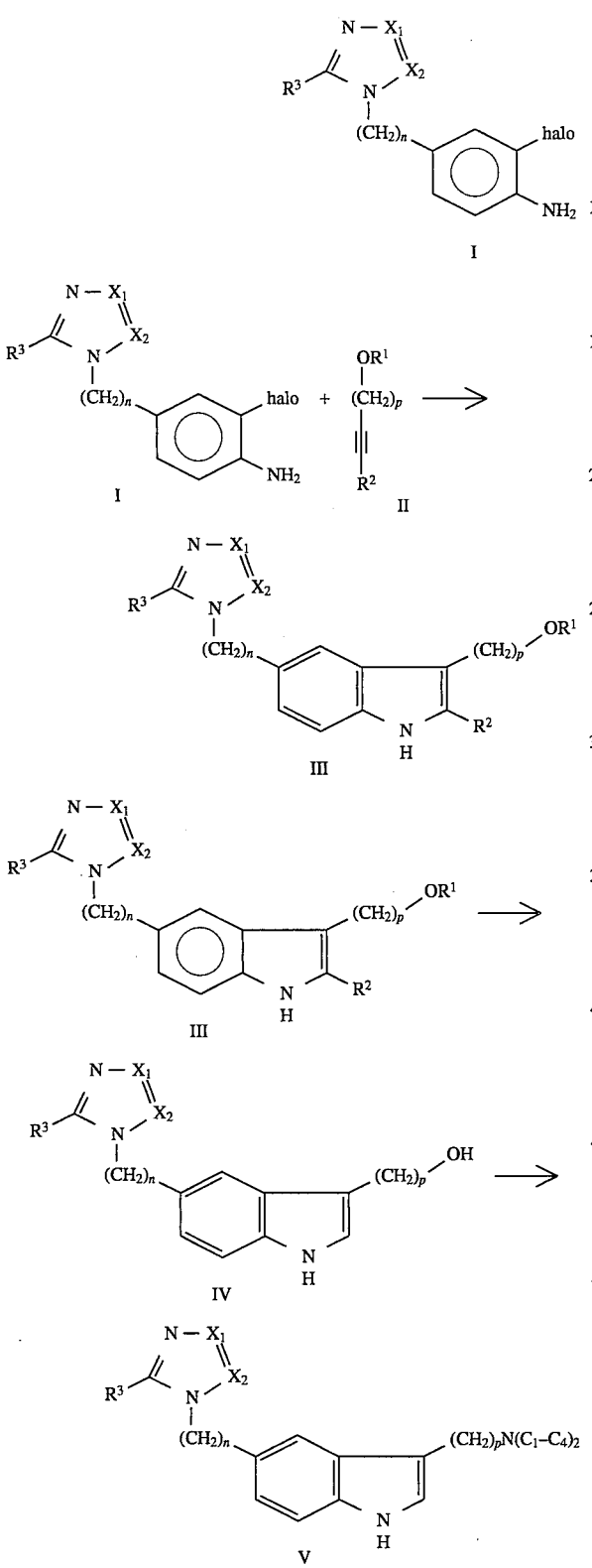

In the beginning step of the process, Structure Ia is reacted with a halogenating agent to form Structure I at a temperature of about −10° to 10° C. in a suitable solvent and in the presence of a suitable proton acceptor.

The halogenating agent can be, for example, iodine monochloride, N-iodosuccinimide, N-bromosuccinimde, and the like. By the term "halo" as used herein is meant Br or I.

The values for "n" are 0, 1 and the values for "p" are 1, 2, 3 and 4.

The solvent in this step can be MeOH, MeOH-H$_2$O, EtOH, THF-H$_2$O, CH$_2$Cl$_2$, and the like, and a useful solvent is 95% MeOH-H$_2$O.

Useful proton acceptors which can be used include: CaCO$_3$, K$_2$CO$_3$, Na$_2$CO$_3$, Li$_2$CO$_3$, LiOH, KOH, NaOH, NaHCO$_3$, and the like. When using N-bromosuccinimide or N-iodosuccinimide, a separate proton acceptor is not required.

A useful set of reaction conditions for the halogenating step is MeOH-H$_2$O (95%), as the solvent, a temperature of about 0° C., whereby the reaction is carried out at atmospheric pressure under an inert atmosphere, e.g., dry N$_2$, in the presence of calcium carbonate.

Structure II, being the protected 1-alkynol, is prepared by reacting the starting 1-alkynol IIa; which can be selected from 2-propyn- 1-ol (propargyl alcohol), 3-butyn-1-ol, 4-pentyn-1-ol, and 5-hexyn-1-ol:

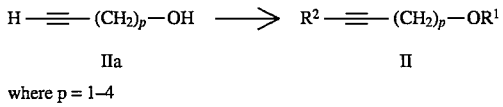

IIa        II where p = 1–4 in a suitable inert organic ether solvent, e.g., tetrahydrofuran, dioxane, diethyl ether, 1,2-dimethoxyethane, and the like, under a dry atmosphere, e.g., dry N$_2$, at a temperature of −50° C. to −10° C. with a slight excess of n-butyllithium, being about 2.1 moles per mole of alkynol for a sufficient time, e.g., 2–8 hours to completely generate the dilithium anion of the alkynol. Then the protecting group is attached by adding a precursor, e.g., chlorotrimethylsilane, in also a slight excess of about 2.1 moles per mole of the lithiumdianion of the alkynol and allowed to stir for 1–4 hours, to complete the reaction. The reaction is worked up by conventional procedures to yield the diprotected alkynol II.

The R$^1$ protecting group can be selectively removed by mild acid hydrolysis, e.g., stirring in about 1:1 by volume 2 N HCl/MeOH at below 30° C., e.g., 0°–30° C., and recovering the product. The resulting alcohol can be selectively protected with another protecting group, R$^1$ following the above-described protecting procedure to derive II, where R$^1$ and R$^2$ are different protecting groups.

The silylating agents which can be used are generally halogenated trihydrocarbyl silanes, e.g., chloro-triethylsilane.

The tetrahydropyranyl, THP, protecting group can be applied by using the starting compound dihydropyran as a precursor, in the presence of an acid catalyst e.g., p-CH$_3$PhSO$_2$OH, to convert the alkynol to the THP ether.

Structure I is then coupled with Structure II to form Structure III via a palladium-catalyzed reaction in a dry inert organic solvent containing a soluble palladium catalyst and in the presence of a proton acceptor, being an aromatic amine, alkylamine or inorganic base, which is not a catalyst poison, at a temperature of about 70° to 120° C.

In the Structure III, R$^3$ is H or C$_1$–C$_4$ linear or branched alkyl, including methyl, ethyl, n-propyl, isopropyl, n-butyl, sec-butyl, isobutyl and t-butyl.

R$^1$ is H, or a hydroxy protecting group selected from: the silyl ligand SiR$^a$$_3$, where each R$^a$ is independently selected from linear or branched C$_1$–C$_4$ alkyl (as described above) or phenyl; and tetrahydropyranyl.

Representative examples of SiR$^a_3$ radicals include trimethylsilyl, triethylsilyl, tributylsilyl, triphenylsilyl, dimethyl-t-butylsilyl, dimethylphenylsilyl, diphenylmethylsilyl, triisopropylsilyl, and the like.

R$^2$ acts as a protecting group for the terminal acetylene carbon and has the same structure SiR$^a_3$ as described above, Both R$^1$ and R$^2$ are removable by mild acid hydrolysis, e.g., contacting with about a 1:1 by volume 2 N HCl/MeOH solvent mixture at about 0°–30° C. for 1–24 hours to completely remove the R$^1$, R$^2$ radicals.

The organic solvent useful in this coupling/ring closure step must be one in which Structure I, Structure II and the palladium-catalyst are soluble and compatible and is chemically inert under the reaction conditions.

Classes of solvents useful in this reaction are N,N-di($C_1$–$C_4$)$C_1$–$C_2$ alkanoamides, $C_4$–$C_8$ linear ethers, $C_4$–$C_6$ cyclic mono or diethers, di $C_1$–$C_4$ alkoxyethanes, $C_6$–$C_{10}$ aromatic hydrocarbons, mono or dichlorinated $C_1$–$C_4$ alkanes, alkylnitriles, and the like, or mixtures thereof.

Representative solvents include: dimethylformamide, dimethylacetamide, diethylether, dipropyl ether, tetrahydrofuran, dioxane, 1,2-dimethoxyethane, benzene, toluene, o-xylene, m-xylene, p-xylene, acetonitrile, propionitrile and the like, or mixtures thereof.

The temperature is carded out in the range of 70° to 120° C. A useful temperature is in the range of about 90°–110° C. Generally, the reaction is carded out under dry $N_2$ at atmospheric pressure.

The palladium catalyst useful in the reaction can be selected for example, from the following classes: Pd alkanoates, Pd acetonates, Pd halides, Pd halide complexes, Pd-benzylidene acetone complexes, and the like. Representative examples include: Pd (II) acetate, Pd (II) acetylacetonate, Pd (O) bis-dibenzylidene acetone, Pd (II) bromide, Pd (II) chloride, Pd (II) iodide, Pd (II) sulfate, Pd (11) trifluoroacetate, Pd (II) $Cl_2(CH_3CN)_2$, and the like. A useful catalyst is palladium acetate.

The palladium catalyst is used in an amount of about 0.5 to 5 mole per cent based on the iodoaniline I and a useful range is about 2 to 3 mole percent of soluble palladium catalyst based on the iodoaniline, I.

The proton acceptor useful in this step is a basic compound which can be organic or inorganic and acts as a proton acceptor and is not a "catalyst poison". By the term "catalyst poison" is meant interaction with the catalyst to inhibit its catalytic activity and prevent the coupling/ring closure between Structure I and II from occurring.

Suitable classes of proton acceptors include alkylamines, aromatic amines, heterocyclic amines, Group I alkali metal and Group II alkaline earth carbonates, bicarbonates, phosphates, bisphosphates, and the like.

Representative compounds include lithium carbonate sodium carbonate, potassium carbonate, sodium bicarbonate, potassium bicarbonate, calcium carbonate, triethylamine, diisopropylethylamine, pyridine, N,N-dimethylaniline, 4-dimethylaminopyridine, and the like.

The removal of the protecting groups R$^1$ and R$^2$ from III is usually accomplished by mild acid hydrolysis without the separate isolation of III. Where the coupling/ring closure is complete, the solvents are generally removed under reduced pressure. A mixture of about 1:1 by volume 2 N HCl/MeOH is added to the concentrate of III at room temperature and the mixture allowed to stir at below 30° C., e.g., 0°–30° C., for about 2–4 hours to completely remove both R$^1$ and R$^2$ protecting groups to obtain IV.

The replacement of hydroxyl in IV with dialkylamine to produce V is generally carried out as a two-step reaction in one reaction vessel.

The alcohol IV can be reacted with mesyl chloride, ($CF_3SO_2)_2$ O, and the like, in a dry inert organic solvent, e.g., tetrahydrofuran, dioxane, diethyl ether, 1,2-dimethoxyethane, dichloromethane, and the like, at about –30° to –10° C., under a dry N2 atmosphere, in the presence of a proton acceptor, being a soluble aliphatic or aromatic amine, e.g., triethylamine, pyridine, diethylmethylamine, diisopropylethylamine, tributylamine, 4-dimethylaminopyridine, and the like to form the intermediate mesylate, or sulfonate, in situ.

The dialkylamine analog V can then prepared by simply adding the dialkylamine to the mesylate reaction vessel contents, and allowing to stir at room temperature for 1 hour.

The obtained Structure V can be isolated as is or reacted with an appropriate pharmaceutically acceptable acid, e.g., HCl, $H_2SO_4$, benzoic acid, succinic acid, lactic acid, maleic acid, and the like, to form the corresponding acid addition salt.

Representative examples of Structure V that can be produced by the process are:

N,N-Dimethyl-2-[5-(1,2,4-triazol-1 -ylmethyl)-1H-indol-3-yl]ethylamine

N,N-Dimethyl-2-[5-(1,3-imidazol-1 -ylmethyl)-1H-indol-3-yl]ethylamine

N,N-Dimethyl-2-[5-(5-methyl-1,2,3,4-triazol-1 -ylmethyl)-1H-indol-3-yl] ethylamine N,N-Dimethyl-2-[5-(1,3,4-triazol-1-ylmethyl)-1H-indol-3-yl]ethylamine N,N-Dimethyl-2-[5-(1,3,4-triazol-1-yl     )-1H-indol-3-yl] ethylamine N,N-Diethyl-2-[5-(1,2,4-triazol-1-ylmethyl)-1H-indol-3-yl] ethylamine N,N-Diethyl-2-[5-(1,3-imidazol-1-ylmethyl)-1H-indol-3-yl]ethylamine N,N-Diethyl-2-[5-(5-methyl-1,2,3,4-tetrazol-1-ylmethyl)-1H-indol-3 -yl]ethylamine N,N-Diethyl-2-[5-(1,3,4-triazol-1-ylmethyl)-1H-indol-3-yl] ethylamine N,N-Diethyl-2-[5-(1,3,4-triazol-1-yl)-1H-indol-3-yl]ethylamine N,N-Dimethyl-[5-(1,2,4-triazol-1-ylmethyl)-1H-indol-3-yl] methylamine N,N-Dimethyl-[5-(1,3-imidazol-1-ylmethyl)-1H-indol-3-yl] methylamine N,N-Dimethyl-[5-(5-methyl-1,2,3,4-tetrazol-1-ylmethyl)-1H-indol-3 -yl]methylamine N,N-Dimethyl-[5-(1,3,4-triazol-1-ylmethyl)-1H-indol-3-yl] methylamine N,N-Dimethyl-[5-(1,3,4-triazol-1-yl)-1H-indol-3-yl]methylamine N,N-Diethyl-3-[5-(1,2,4-triazol-1-ylmethyl)-1H-indol-3-yl] propylamine N,N-Dimethyl-3-[5-(1,3-imidazol-1-yl)-1H-indol-3-yl]propylamine N,N-Diethyl-3-[5-(5-methyl-1,2,3,4-tetrazol-1-ylmethyl)-1H-indol-3 -yl]propylamine N,N-Dimethyl-3-[5-(1,3,4-triazol-1-ylmethyl)-1H-indol-3-yl]propylamine N,N-Diethyl-3-[5-(1,3,4-triazol-1-yl)-1H-indol-3-yl]propylamine N,N-Dimethyl-4-[5-(3-methyl-1,2,4,5-tetrazol-1-ylmethyl)-1H-indol-3 -yl]butylamine N,N-Dimethyl-4-[5-(2-ethyl-1,3-ethyl-imidazol-1-ylmethyl)-1H-indol-3 -yl]butylamine N,N-Dimethyl-4-[5-(5-ethyl-1,2,3,4-triazol-1-ylmethyl)-1H-indol-3 -yl]butylamine N,N-Dimethyl-4-[5-(2-methyl-1,3,4-triazol-1-ylmethyl)-1H-indol-3 -yl]butylamine N,N-Dimethyl-4-[5-(2-ethyl-1,3,4-triazol-1-yl)-1H-indol-3-yl]butylamine.

Also included are the alcohol analogs of the above amines, including, e.g.,

2-[5-(1,2,4-triazol-1-ylmethyl)-1H-indol-3-yl]ethylalcohol
2-[5-(1,3-imidazol-1-ylmethyl )-1H-indol-3-yl]ethylalcohol
2-[5-(5-methyl-1,2,3,4-tetrazol-1-ylmethyl)-1H-indol-3-yl]ethylalcohol
2-[5-(1,3,4-triazol-1-ylmethyl)-1H-indol-3-yl]ethylalcohol
2-[5-(1,3,4-triazol-1-yl)-1H-indol-3-yl]ethylalcohol
[5-(1,2,4-triazol-1-ylmethyl)-1H-indol-3-yl]-methylalcohol
3-[5-(1,3-imidazol-1-ylmethyl)-1H-indol-3-yl]propylalcohol
4-[5-(5-methyl-1,2,3,4-tetrazol-1-ylmethyl)-1H-indol-3-yl]butylalcohol
2-[5-(2-methyl-1,3,4-triazol-1-ylmethyl)-1H-indol-3-yl]ethylalcohol
2-[5-(5-methyl-1,3,4-triazol-1-yl)-1H-indol-3-yl]ethylalcohol The following examples are illustrative of the invention as contemplated by the inventors and should not be construed to limit the scope or spirit of the instant invention.

EXAMPLE 1

Step 1

Preparation of Iodoaniline 3

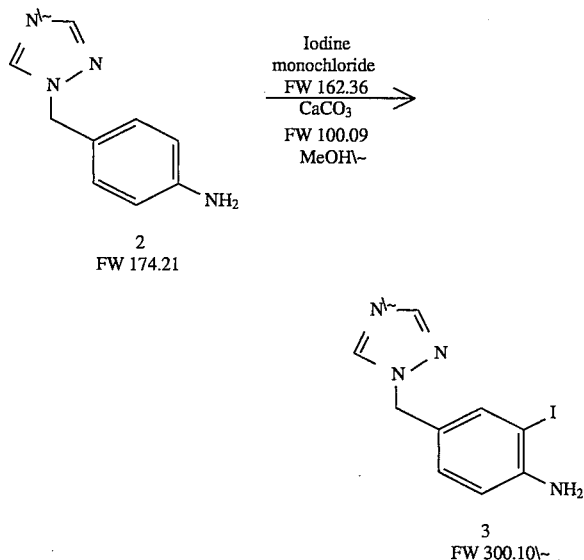

| Materials | Amount | Mol | MW |
|---|---|---|---|
| Aniline 2 | 30.0 g | 0.17 | 174.21 |
| Iodine monochloride | 30.3 g | 0.19 | 162.3 |
| Calcium carbonate | 34.0 g | 0.34 | 100.09 |
| Methanol | 240 mL | | |
| Ethyl acetate | 350 mL | | |

To a mixture of powdered calcium carbonate (34 g, 0.34 mol) and aniline 2 (30.0 g, 0.17 mol) in methanol (240 mL) and water (12 mL) at 0° C. under nitrogen is added a solution of iodine monochloride (30.3 g, 0.19 mol) in methanol (120 mL) over 0.5 h.

The mixture is warmed to room temperature and quenched with half-saturated sodium thiosulphate solution (5 mL). The mixture is stirred for 30 min. The solids are filtered and washed with ethyl acetate (100 mL).

The filtrate is concentrated in vacuo to 100 mL, diluted with ethyl acetate (250 mL), washed with half-saturated sodium thiosulphate (200 mL), dried with magnesium sulfate and concentrated to 100 mL. Hexanes is added to precipitate the iodoaniline 3 as a pale-tan solid (48.5 g, 91%).

Recrystallization of the iodoaniline 3 (24 g) from ethanol affords the iodoaniline 3 (14.5 g, 60% recovery) as a white powder: mp 114°–115° C.

Step 2

Protection of Butynol as bis-Triethylsilyl-butynol

5a

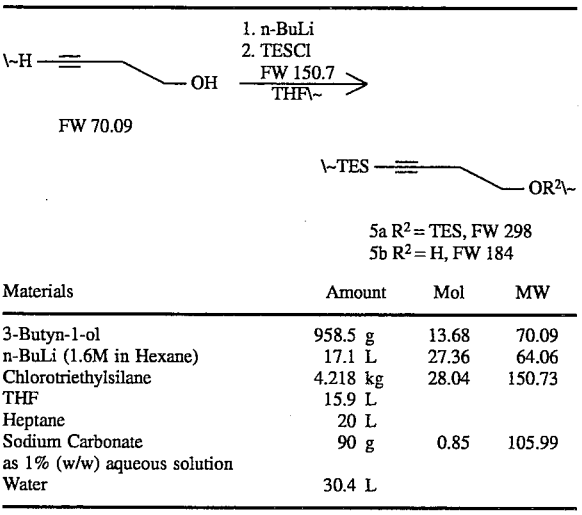

| Materials | Amount | Mol | MW |
|---|---|---|---|
| 3-Butyn-1-ol | 958.5 g | 13.68 | 70.09 |
| n-BuLi (1.6M in Hexane) | 17.1 L | 27.36 | 64.06 |
| Chlorotriethylsilane | 4.218 kg | 28.04 | 150.73 |
| THF | 15.9 L | | |
| Heptane | 20 L | | |
| Sodium Carbonate as 1% (w/w) aqueous solution | 90 g | 0.85 | 105.99 |
| Water | 30.4 L | | |

Dry tetrahydrofuran (15.9 L) is charged to a flask fitted with a mechanical stirrer and thermocouple under a nitrogen atmosphere and 3-butyn-1-ol (958.5 g, 13.68 mol) is charged to the flask. The mixture is cooled to –30° C. and n-BuLi (17.1 L, 27.36 mol) is added dropwise over 4 h, keeping the temperature below –20° C.

The mixture is aged at –20° C. for 1.2 h. Chlorotriethylsilane (4.218 kg, 28.04 mol) is added dropwise over 55–60 min, keeping the reaction temperature below –10° C. The mixture is then allowed to warm to room temperature. The reaction is complete after 1.5 h at approximately 22° C.

The solution is cooled to –10° C. and 1% (w/w) Na$_2$CO$_3$ (8.4 L) is added over 25 min at <0° C. Heptane (10 L) is added and the layers are partitioned. The aqueous layer is extracted with heptane (10 L). The combined organic layers are washed with water (22 L) and concentrated to a pale orange-yellow oil to afford product 5a (98.1% yield, 93.8 wt % purity).

Step 3

Palladium-catalyzed Coupling to Prepare Tryptophol 7

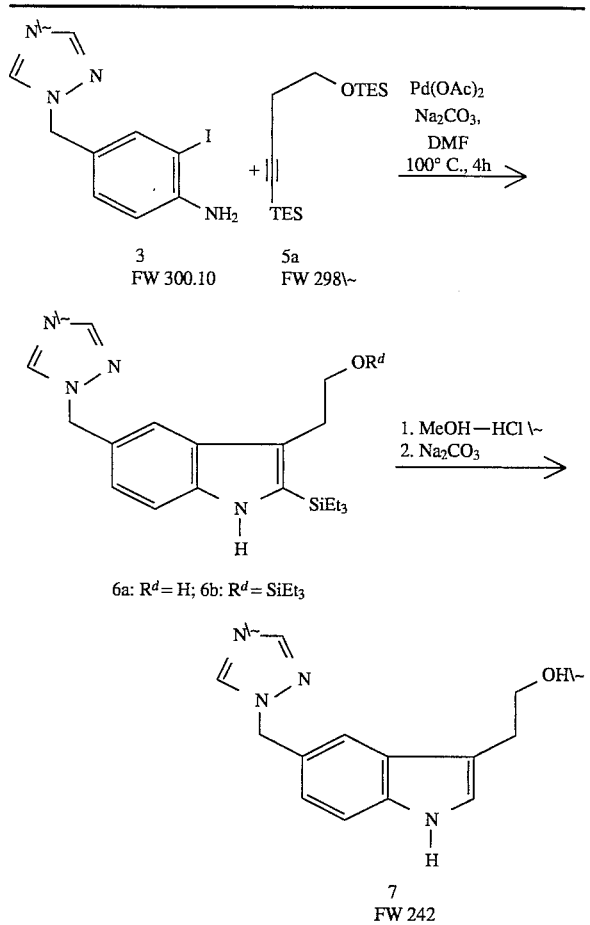

| Materials | Amount | mMol | MW |
|---|---|---|---|
| Iodoaniline 3 | 9 g | 30 | 300.10 |
| bis-TES-butynol 5a (40 W %) | 24.5 g | 31.5 | 298 |
| Palladium acetate | 134.4 mg | 0.6 | 224.5 |
| Sodium carbonate (powdered) | 15.9 g | 150.0 | 105.9 |
| Dimethylformamide | 120 mL | | |
| Solka-Floc | 2 g | | |
| Isopropyl acetate | 365 mL | | |
| Water | 100 mL | | |
| Methanol | 35 mL | | |
| 2N HCl | 30 mL | | |
| Heptane | 70 mL | | |
| Saturated Na₂CO₃ | 24 mL | | |
| Darco G-60 | 0.5 g | | |
| IPAc/Heptane (1:2) | 36 mL | | |

To dry dimethylformamide (12 mL) is charged a solution of bis-TES-butynol 5a in heptane (24.5 g, 31.5 mmol, 40% by wt). The mixture is concentrated under vacuum to a volume of 22 mL. To this concentrate is charged dimethylformamide (78 mL), iodoaniline 3 (9 g, 30 mmol), and powdered sodium carbonate (15.9 g, 0.15 mol). The mixture is degassed with vacuum/nitrogen purges.

Palladium acetate (134.4 mg, 0.6 mmol) is added and the mixture is heated at 100° C. for 4 h.

The product mixture is cooled to room temperature and filtered through Solka-Floc. The cake is washed with dimethylformamide (30 mL). The combined filtrate and wash are distilled at 26 mmHg (bp for DMF: 67° C.) to ~25 mL to remove ~100 mL of distillate. Isopropyl acetate (IPAC) (150 mL) and water (50 mL) are added to the distillation residue. The resultant mixture is filtered through 2 g of Solka-Floc and the cake is washed with isopropyl acetate (15 mL). The combined filtrates are washed with water (50 mL) and concentrated to 50 mL.

The above concentrate is diluted with methanol (35 mL) and 2N HCl (30 mL, 2 eq) is added over 20 min, keeping the reaction temperature below 30° C. The mixture is aged at room temperature for 2 hours or until the reaction is complete.

Heptane (36 mL) is added and the heptane-isopropyl acetate layer is separated. The methanol-water layer containing the product 7 is concentrated in vacuo to 65 mL with the removal of methanol (20 mL).

Isopropyl acetate (50 mL) is added to the mixture. The mixture is cooled to 18° C. followed by the addition of saturated aqueous sodium carbonate (24 mL) over 10 min. Isopropyl acetate (50 mL) is added to the mixture. The aqueous layer is separated and extracted with isopropyl acetate (100 mL). The combined organic solution (200 mL) is treated with Darco G-60 (0.5 g). The mixture is stirred for 5 h and filtered. The tiltrate is concentrated to 100 mL to give a thin slurry, followed by the addition of heptane (34 mL). The slurry is aged at room temperature for 1 h. The solid is filtered and washed with heptane/isopropyl acetate (2:1; 36 mL). The product is dried to afford the tryptophol 7 (5.5 g, 75%). The NMR data and C,H,N analytical data is presented above on "References and Notes".

Step 4

MK-0462 Free Base

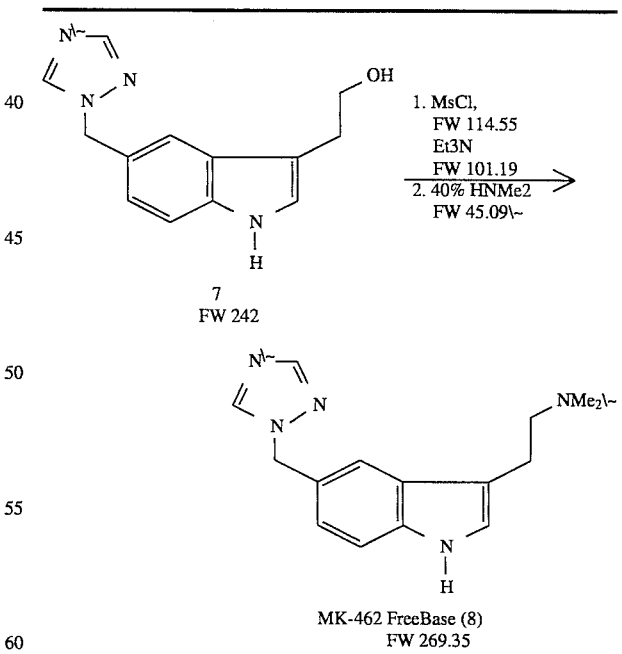

| Materials | Amount | Mol | MW |
|---|---|---|---|
| Tryptophol 7 | 4.87 g | 0.0201 | 242.28 |
| Methanesulfonyl chloride | 2.30 g | 0.0201 | 114.55 |
| Triethylamine | 2.64 g | 0.0261 | 101.19 |
| Tetrahydrofuran | 97 mL | | |
| Aqueous dimethylamine | 49 mL | 0.39 | 45.09 |

| | |
|---|---|
| (40% w/w) | |
| Aqueous potassium carbonate (saturated) | 15 mL |
| Isopropyl acetate | 100 mL |
| Darco G-60 | 0.48 g |
| Heptane | 64 mL |

The tryptophol 7 (4.87 g) is slurried in dry tetrahydrofuran (97 mL) and sieve-dried triethylamine (2.64 g, 26.1 mmol) is added. The slurry is cooled to −20° C. and methanesulfonyl chloride (2.30 g, 20.1 mmol) is added at <−15° C. over 45 min. The reaction mixture is aged for 30 min, at −20° C.

The slurry is filtered at <−15° C. and the filter cake is washed with cold, dry tetrahydrofuran (25 mL).

Aqueous dimethylamine (40% w/w, 49 mL, 0.39 mol) is added to the combined filtrates. The reaction mixture is allowed to warm to room temperature.

Most of the THF is removed by distillation under vacuum at <30° C. (final volume 60 mL). Isopropyl acetate (50 mL) and saturated aqueous potassium carbonate (5 mL) are added. The layers are well-mixed and separated. The aqueous layer is extracted with isopropyl acetate (50 mL).

The combined organic layers are washed with saturated aqueous potassium carbonate (10 mL). Isopropyl acetate (20 mL) is added to the diluted organic layer and the product solution is dried by heating under reflux over a Dean/Stark trap. The solution is cooled and treated with Darco G60 (0.5 g) for 60 min, and the mixture is filtered. The filtrates are concentrated to 20 mL by distillation under vacuum, seeded and then allowed to crystallize for >1 h. Heptane (64 mL) is added to the seed bed over 1 hour and the slurry is cooled to 0° C. After a 1 hour age the slurry is filtered. The product is washed with cold 4:1 heptane-isopropyl acetate (2×10 mL) and dried in a vacuum at 40° C. The free base of MK-0462 (8) is obtained as a cream-colored solid (4.30 g, 73% yield). The NMR and C,H,N analytical data is presented above on "References and Notes".

Step 5

Formation of MK-0462 Benzoate

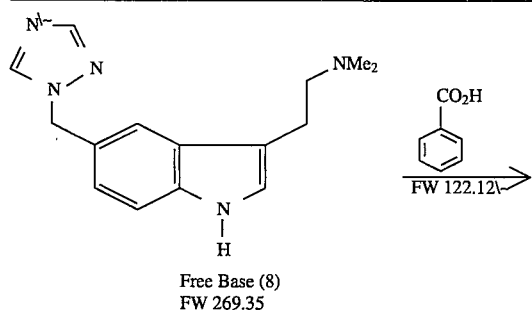

Free Base (8)
FW 269.35

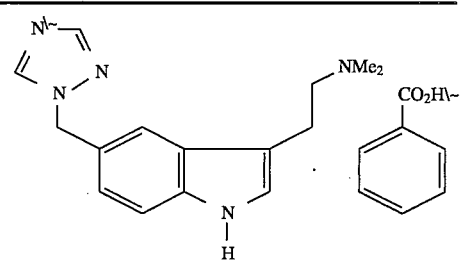

Benzoate MK-462 (1)
FW 391.47

| Materials | Amount | mMol | MW |
|---|---|---|---|
| MK-0462 Free base (89 wt % purity) | 10 g | 33.0 | 269.35 |
| Benzoic Acid | 4.5 g | 36.8 | 122.12 |
| Isopropanol | 80 mL | | |
| Isopropyl acetate | 30 mL | | |

To a solution of MK-0462 free base (10 g, 89 wt % pure) in isopropyl alcohol (80 mL) at room temperature is added a solution of benzoic acid (4.5 g, 36.8 mmol) in isopropyl acetate (20 mL) over 10 min. The mixture is aged at room temperature for 0.5 h, cooled to 0°–5° C. and filtered. The cake is washed with isopropyl acetate (10 mL) and dried to give crude MK-0462 benzoate salt (13.1 g, 95 wt % pure, 96% assay yield). Recrystallized from EtOH to yield pure solid material. The elemental analysis and analytical spectra were consistent with the proposed structure.

What is claimed is:

1. A process comprising the step of contacting a compound of Structure I with a compound of Structure II to form a compound of Structure III:

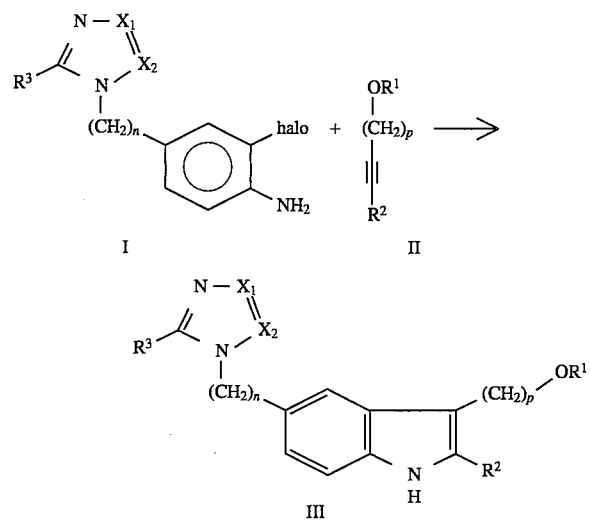

said process being carried out in an organic solvent at a temperature in the range of about 70° to 120° C., in the presence of a soluble palladium catalyst, and in the presence of an inorganic or organic amine compound which functions as a proton acceptor and does not chemically react with said catalyst, wherein:

$X_1$ and $X_2$ are independently ring nitrogen or carbon atoms;

halo represents Br or I;

n is an integer from 0–1;

p is an integer from 1–4;

$R^3$ is H or linear or branched $C_1$–$C_4$ alkyl;

$R^1$ is H or a radical which functions as a hydroxy protecting group, and $R^2$ is a radical which functions as a terminal acetylene carbon protecting group, wherein said process is conducted in the absence of triphenylphosphine, lithium chloride or tetrabutyl ammonium chloride.

2. The process of claim 1 wherein only one of $X_1$, $X_2$ is a ring nitrogen.

3. The process of claim 1 wherein halo is I.

4. The process of claim 1 wherein n is 1 and p is 2.

5. The process of claim 1 wherein $R^1$ is selected from the group consisting of: H; $SiR^a_3$, where each $R^a$ is independently selected from linear or branched $C_1$–$C_4$ alkyl or phenyl; or tetrahydropyranyl; and $R^2$ is selected from $SiR^a_3$, where $R^a$ is defined herein.

6. The process of claim 5 wherein said SiRa3 radical is selected from trimethylsilyl, triethylsilyl, tributylsilyl, triphenylsilyl, dimethyl-t-butylsilyl, dimethylphenylsilyl, diphenylmethylsilyl and triisopropylsilyl.

7. The process of claim 1 wherein said solvent is selected from N,N-di($C_1$–$C_4$) $C_1$–$C_2$ alkanoamides, $C_4$–$C_8$ linear ethers, $C_4$–$C_6$ cyclic mono or diethers, di $C_1$–$C_4$ alkoxy ethanes, $C_1$–$C_{10}$ aromatic hydrocarbons, mono or dichlorinated $C_1$–$C_4$ alkanes or alkyl nitriles.

8. The process of claim 7 wherein said solvent is DMF.

9. The process of claim 1 wherein said temperature is in the range of about 90° to 110° C.

10. The process of claim 1 wherein said palladiumcatalyst is a palladium alkanoate, palladium halide, palladium acetonate, palladium halide complex or palladium benzylidene acetone complex.

11. The process of claim 10 wherein said palladiumcatalyst is palladium acetate.

12. The process of claim 1 wherein said palladiumcatalyst is present in an amount of 0.5 to 5 mole percent relative to the Structure I.

13. The process of claim 1 wherein said proton acceptor is selected from Group I alkali and Group II alkaline earth metal carbonates, bicarbonates, phosphates, bisphosphates, $C_1$–$C_4$ trialkylamines, aromatic amines and heterocyclic amines.

14. The process of claim 13 wherein said proton acceptor is sodium carbonate.

15. The process of claim 1 carded out in the absence of triphenylphosphine.

16. The process of claim 1 further comprising the step of: contacting a compound of Structure Ia.

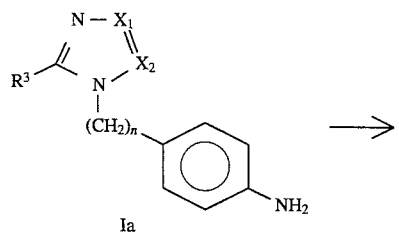

with a halogenating agent to form Structure I.

17. The process of claim 16 further comprising the step of treating a compound of Structure III with mild acid hydrolysis to form a compound of Structure IV:

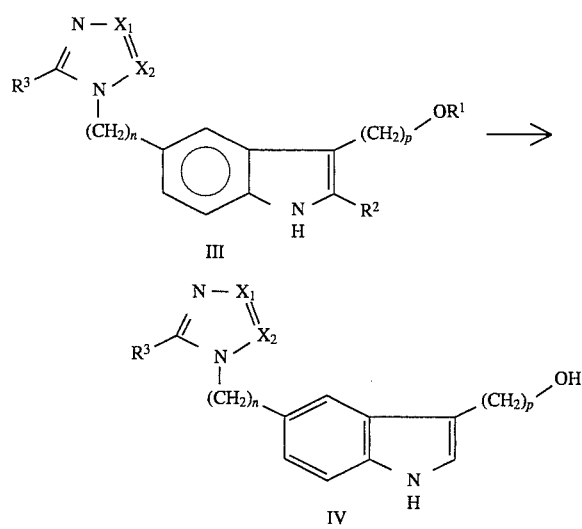

18. The process of claim 17 further comprising the step of contacting a compound of Structure IV first with an alkylsulfonyl chloride, then with a di $C_1$–$C_4$ alkylamine to form a compound of Structure V:

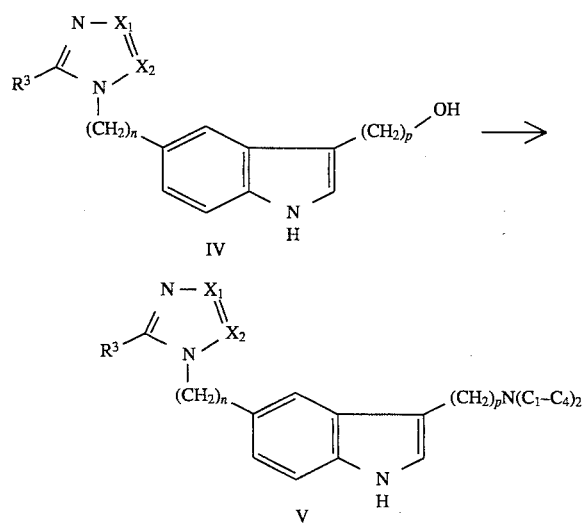

19. The process of claim 18 wherein Structure V is:
N,N-Dimethyl-2-[5-(1,2,4-triazol-1-ylmethyl)-1H-indol-3-yl]ethylamine
N,N-Dimethyl-2-[5-(1,3-imidazol-1-ylmethyl)-1H-indol-3-yl]ethylamine N,N-Dimethyl-2-[5-(5-methyl-1,2,3,4-triazol-1-ylmethyl)-1H-indol-3yl]ethylamine N,N-Dimethyl-2-[5-(1,3,4-triazol-1-ylmethyl)-1H-indol-3-yl]ethylamine N,N-Dimethyl-2-[5-(1,3,4-triazol-1-yl)-1H-indol-3-yl]ethylamine N,N-Diethyl-2-[5-(1,2,4-triazol-1-ylmethyl)-1H-indol-3-yl]ethylamine N,N-Diethyl-2-[5-(1,3-imidazol-1-ylmethyl)-1H-indol-3-yl]ethylamine N,N-Diethyl-2-[5-(5-methyl-1,2,3,4-tetrazol-1-ylmethyl)-1H-indol-3yl]ethylamine N,N-Diethyl-2-[5-(1,3,4-triazol-1-ylmethyl)-1H-indol-3-yl]ethylamine N,N-Diethyl-2-[5-(1,3,4-triazol-1-yl)-1H-indol-3-yl]ethylamine N,N-Dimethyl-[5-(1,2,4-triazol-1-ylmethyl)-1H-indol-3-yl]methylamine N,N-Dimethyl-[5-(1,3-imidazol-1-ylmethyl)-1H-indol-3-yl]methylamine N,N-Dimethyl-[5-(5-methyl-1,2,3,4-tetrazol-1-ylmethyl)-1H-indol-3-yl]methylamine N,N-Dimethyl-[5-(1,3,4-triazol-1-ylmethyl)-1H-indol-3-yl]methylamine N,N-Dimethyl-[5-(1,3,4-triazol-1-yl)-1H-indol-3-yl]methylamine N,N-Diethyl-3-[5-(1,2,4-triazol-1-ylmethyl)-1H-indol-3-yl]propylamine N,N-Dimethyl-3-[5-(1,3-imidazol-1-yl)-1H-indol-3-yl]propylamine N,N-Diethyl-3-[5-(5-methyl-1,2,3,4-tetrazol-1-ylmethyl)-1H-indol-3-yl]propylamine N,N-Dimethyl-3-[5-(1,3,4-triazol-1-ylmethyl)-1H-indol-3-yl]propylamine N,N-Diethyl-3-[5-(1,3,4-triazol-1-yl)-1H-indol-3-yl]propylamine N,N-Dimethyl-4-[5-(3-methyl-1,2,4,5-tetrazol-1-ylmethyl)-1H-indol-3-yl]butylamine N,N-Dimethyl-4-[5-(2-ethyl-1,3-ethyl-imidazol-1-ylmethyl)-1H-indol-3-yl]butylamine N,N-Dimethyl-4-[5-(5-ethyl-1,2,3,4-triazol-1-ylmethyl)-1H-indol-3-yl]butylamine N,N-Dimethyl-4-[5-(2-methyl-1,3,4-triazol-1-ylmethyl)1H-indol-3-yl]butylamine N,N-Dimethyl-4-[5-(2-ethyl-1,3,4-triazol-1-yl)-1H-indol-3-yl]butylamine 20. The process of claim 19 wherein Structure V is N,N-dimethyl-2-[5-(1,2,4-triazol-1-ylmethyl)-1H-indol-3-yl]ethylamine.

21. The process of claim 18 wherein:

(a) Compound 2 is contacted with iodine monochloride in

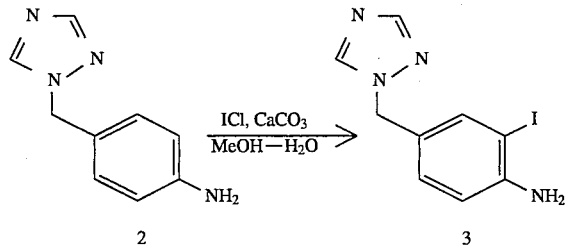

95% MeOH/$H_2O$ in the presence of calcium carbonate at 0° C. under nitrogen to produce Compound 3;

(b) Compound 3 is contacted with Compound 5a in dry DMF containing Pd(OAc)$_2$ and sodium carbonate,

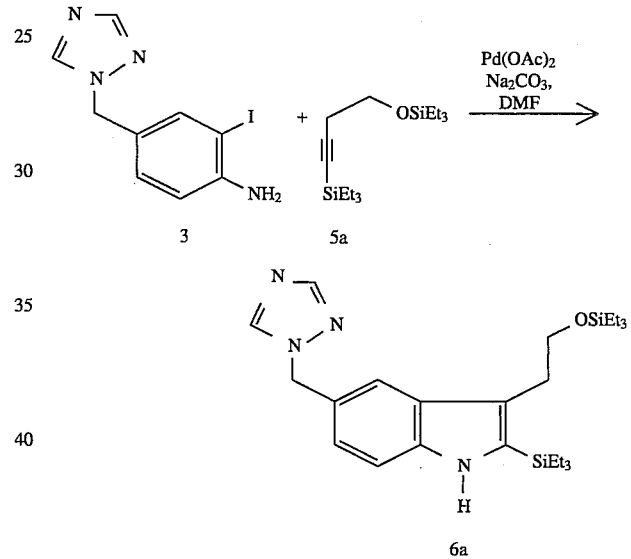

at about 100° C. for a sufficient time to produce Compound 6a;

(c) Compound 6a is contacted with about a 1:1 by volume 2N HCl/MeOH mixture at 0°–30° C. for a

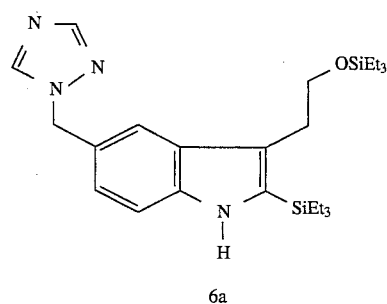

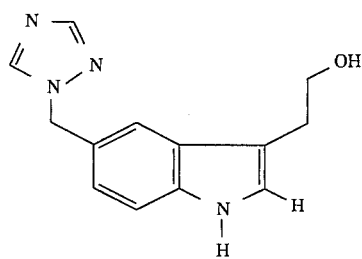

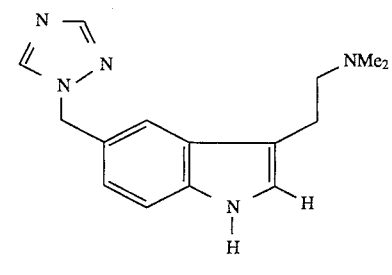

sufficient time to remove the SiEt₃ protecting groups and form Compound 6;

(d) Compound 7 is contacted with mesylchloride in dry tetrahydrofuran at −20° C. containing triethylamine under dry nitrogen for a sufficient time to form an intermediate mesylate in situ:

and then contacted with 40% aqueous dimethylamine and the mixture allowed to react for a sufficient time to form Compound 8.

\* \* \* \* \*